US006451545B2

(12) United States Patent
Tanaka et al.

(10) Patent No.: US 6,451,545 B2
(45) Date of Patent: Sep. 17, 2002

(54) MONOCLONAL ANTIBODY SPECIFIC TO ANTI-HUMAN FIBRIN MONOMER, PROCESS FOR PRODUCING THE SAME, HYBRIDOMAS, AND IMMUNOASSAY METHOD

(75) Inventors: Seiji Tanaka, Ibaraki (JP); Akiei Hamano, Ibaraki (JP); Mamoru Umeda, Ibaraki (JP)

(73) Assignee: Nissui Pharmaceutical Co., Ltd. (JP)

( * ) Notice: Subject to any disclaimer, the term of this patent is extended or adjusted under 35 U.S.C. 154(b) by 56 days.

(21) Appl. No.: 09/242,469

(22) PCT Filed: Jun. 19, 1998

(86) PCT No.: PCT/JP98/02733

§ 371 (c)(1),
(2), (4) Date: Feb. 17, 1999

(87) PCT Pub. No.: WO98/59047

PCT Pub. Date: Dec. 30, 1998

(30) Foreign Application Priority Data

Jun. 24, 1997  (JP) .............................................. 9-183114

(51) Int. Cl.⁷ ..................... G01N 33/543; G01N 33/577
(52) U.S. Cl. ..................... 435/7.2; 530/387.1; 530/387; 530/388; 530/388.25; 530/391.5; 530/389.3; 530/391.7; 530/388.1; 435/6; 435/7; 435/7.21; 435/7.24; 435/7.92; 435/7.94; 435/240.27; 435/337; 435/7.1; 435/7.9; 435/7.95; 435/13; 435/962; 435/972; 435/975; 435/328; 435/326; 435/346; 435/172.2; 435/23; 435/66; 435/2; 435/68; 435/70; 435/188.7; 436/518; 436/548; 436/69; 436/527; 436/530; 436/531; 436/808; 436/547; 436/66; 436/542; 436/543; 436/544; 424/181.1; 424/179.1; 424/178.1; 424/145.1; 424/183.1; 424/158.1; 424/184.1; 424/1.1; 424/85

(58) Field of Search ............................... 435/6, 7, 7.21, 435/7.24, 7.92, 7.94, 240.27, 337, 7.1, 7.9, 7.95, 13, 962, 972, 975, 328, 346, 172.2, 23, 66, 2, 68, 70, 186.7, 326; 436/518, 548, 69, 527, 530, 531, 808, 547, 66, 542–545, 540, 387, 388, 387.1; 530/388.25, 391.5, 389.3, 391.1, 387.2, 391.7, 388.1; 424/179.1, 178.1, 181.1, 145.1, 183.1, 158.1, 184.1, 1.1, 85; 935/95, 102–104, 106–108, 110

(56) References Cited

U.S. PATENT DOCUMENTS

| | | | | |
|---|---|---|---|---|
| 4,851,334 A | * | 7/1989 | Kudryk et al. | .................. 435/7 |
| 5,175,087 A | * | 12/1992 | Ranby et al. | .................. 435/13 |
| 5,453,359 A | * | 9/1995 | Gargan et al. | ................. 435/13 |
| 5,721,122 A | * | 2/1998 | Gargan et al. | ............ 435/70.21 |
| 5,723,126 A | * | 3/1998 | Gargan et al. | ............ 424/145.1 |
| 5,821,068 A | * | 10/1998 | Soe et al. | .................. 435/7.21 |
| 5,837,540 A | * | 11/1998 | Gargan et al. | ............. 435/337 |
| 5,843,690 A | * | 12/1998 | Gargan | ....................... 435/13 |

FOREIGN PATENT DOCUMENTS

| | | | | |
|---|---|---|---|---|
| EP | 842 949 A1 | 5/1998 | ........... C07K/16/18 |
| JP | 8-301900 A | * | 11/1996 | ........... C07K/16/36 |

OTHER PUBLICATIONS

G.Soe et. al., A monoclonal antibody that recognizes a neo–antigen exposed in the E domain of fibrin monomer complexed with fibrinogen or its derivatives: It's application to the measurement of soluble fibrin in plasma, Blood, vol.88(6), Sep. 1996.*

Patent Abstracts of Japan, 8–301900 A, Nov. 19, 1996 (K.K. Shima Kenkyusho).

H. Lill et al., "A New Immunoassay for Soluble Fibrin Enables a More Sensitive Detection of the Activation State of Blood Coagulation in Vivo", Blood Coagulation and Fibrinolysis, vol. 4, 97–102. 1993.

C.E. Dempfle et al. "Binding of a New Monoclonal Antibody Against N–Terminal Heptapeptide of Fibrin α–Chain to Fibrin Polymerization Site 'A': Effects of Fibrinogen and Fibrinogen Derivatives, and Pretreatment of Samples with NaSCN", Blood Coagulation and Fibrinolysis, vol. 4, 1993, pp. 79–86.

C.E. Dempfle et al., "Comparison of Immunological and Functional Assays for Measurement of Soluble Fibrin", Thrombosis and Haemostasis, vol. 74(2), 1995, pp. 673–679.

S.A. Pfitzner et al. "Fibrin Detected in Plasma of Patients with Disseminated Intravascular Coagulation by Fibrin–Specific Antibodies Consists Primarily of High Molecular Weight Factor xIIIa–Crosslinked and Plasma–Modified Complexes Partially Containing Fibrino Peptide A", Thrombosis and Haemostasis, vol. 78(3), Sep. 1997, pp. 1069–1078.

K. Kurosawa "Kazuko Kuroso", Development of a New Assay Method of DD/E Complex and Its Antigenic Degradation During Fibrinolytic Process, Journal of Tokyo Medical College, vol. 44(5) Sep. 1986, pp. 860–871.—Abstract Only LVC Jan. 14, 2000.

(List continued on next page.)

Primary Examiner—Christopher L. Chin
Assistant Examiner—Lisa V. Cook
(74) Attorney, Agent, or Firm—Lorusso & Loud

(57) ABSTRACT

Provided are a monoclonal antibody making it possible to detect a native fibrin monomer, which is produced at the initial state of blood coagulation, and soluble fibrin; a hybridoma; and an immunoassay for detecting the initial stage of blood coagulation with high sensitivity, quickly, using the monoclonal antibody. Using a fibrinogen analog in blood as an immune source, cell fusion is carried out to prepare a monoclonal antibody which is not reactive with fibrinogen and is specifically and simultaneously reactive with a native fibrin monomer (that is, a fibrin monomer which is present in a body fluid, in particular in blood, and is not solubilized) and soluble fibrin. The fibrin monomer analog is preferably fibrinogen treated with bathroxobin, which is a snake venom.

9 Claims, 1 Drawing Sheet

OTHER PUBLICATIONS

G. Soe et al., "A Monoclonal Antibody that Recognizes a Neo–Antigen Exposed in the E Domain of Fibrin Monomer Complexed with Fibrogen or Its Derivatives: Its Application to the Measurement of Soluble Fibrin in Plasma", Blood, vol. 88(6), Sep. 1996, pp. 2109–2117.

S. Halvorsen et al.: "Thrombin treated plasma employed as a standard for determination of soluble fibrin." Thrombosis Research, vol. 72, No. 4, Nov. 15, 1993.

W. Niewenhuiszen et al.: "A rapid monoclonal antibody–based enzyme immunoassay (EIA) for the quantitative determination of soluble fibrin in plasma." Thrombosis and Haemostasis, vol. 68, No. 3, Sep. 7, 1992.

H. Lill et al.: "A new immunoassay for soluble fibrin enables a more sensitive detection of the ctivation state of blood coagulation in vivo." Blood Coagulation and Fibrinolysis, vol. 4, No. 1, Feb. 1993.

C. Dempfle et al.: "Binding of a new monoclonal antibody against N–terminal heptapeptide of fibrin alpha–chain to fibrin polymerization site 'A': effects of fibrinogen and fibrinogen derivatives, and pretreatment of samples with NaSCN." Blood Coagulation and Fibrinolysis, vol. 4, No. 1, Feb. 1993.

EP 0 678 524 A (Iatron Laboratories, Inc.) Oct. 25, 1995.

* cited by examiner

MONOCLONAL ANTIBODY SPECIFIC TO ANTI-HUMAN FIBRIN MONOMER, PROCESS FOR PRODUCING THE SAME, HYBRIDOMAS, AND IMMUNOASSAY METHOD

This application was filed under 35 USC 371 as the U.S. National Phase of PCT/JP98/02733 and claims priority of Japanese Application 09-183114 filed Jun. 24, 1997.

FIELD OF THE INVENTION

The present invention relates to a monoclonal antibody which is not reactive with fibrinogen and is specifically reactive with a fibrin monomer. In an assay of fibrin in a body fluid, the monoclonal antibody is specifically reactive with a native fibrin monomer which is present in the body fluid without solubilizing, i.e. without cleavage of the fibrin, and is also specifically reactive with soluble fibrin. The invention also relates to an assay for detecting blood coagulation, without interference by various decomposition products of fibrin or of fibrinogen, using the monoclonal antibody.

BACKGROUND OF THE INVENTION

A blood clot in a blood vessel is harmful to a living body, and thus detection of blood coagulation is useful for early diagnosis of various diseases.

In blood coagulation, fibrinogen is affected by active thrombin and consequently fibrinopeptide A, at the side of the N terminal of the α-chain in the fibrinogen, is cleaved to form desAA-fibrin (desAA-Fbn), another name of which is fibrin I (Fbn-I).

Subsequently, fibrinopeptide B at the N-terminal of the β-chain therein is cleaved to form desAABB-fibrin (desAABB-Fbn), another name of which is fibrin II (Fbn-II). The generic name "fibrin monomers" is given to desAA-fibrin and desAABB fibrin.

The formed fibrin monomer is then coagulated and crosslinked to produce fibrin clots. It is known that the period before clotting, when the fibrin monomer is present as an independent monomer in blood, is generally very short, and the fibrin monomer is associated with various proteins in blood, including fibrinogen, to be solubilized, that is, to form soluble fibrin.

C. E. Dempfle et al., (Blood coagulation and Fibrinolysis, 4: 79–86, 1993) reported an antibody obtained by causing thrombin to act on fibrinogen so as to cleave the fibrinopeptide A and then using the resultant N-terminal of the α-chain as an immune source, and a method for measuring fibrin, using this antibody. However, the N-terminal of the α-chain of fibrin is concealed by the interaction thereof with various blood proteins, including fibrinogen in blood, thus resulting in a drawback that the aforementioned antibody cannot react with soluble fibrin in blood.

H. Lill et al., (Blood coagulation and Fibrinolysis, 4: 97–102, 1993) suggested, as an assay for soluble fibrin in blood, a method of solubilizing soluble fibrin by chaotropic ions at a high concentration or the like to make the soluble fibrin into a fibrin monomer, and then measuring the resultant fibrin monomer. In this method, however, a reaction time is necessary for the solubilization for converting the soluble fibrin into the fibrin monomer. Thus, this measurement is not efficient. Moreover, a substance to be detected is diluted by the solubilization, resulting in a drawback that measurement sensitivity decreases.

G. Soe et al., (WO 95/12617; Blood 88(6): 2109–2117, 1996) suggested a method for assaying soluble fibrin without performing any pretreatment, such as solubilization for converting soluble fibrin into a fibrin monomer, and reported a monoclonal antibody which can directly recognize soluble fibrin for this method. The monoclonal antibody according to C. Soe et al., is a monoclonal antibody obtained by solubilizing fibrin clots by urea and then using the resultant urea-solubilized fibrin monomer as an immune source, and is a monoclonal antibody for recognizing a three dimensional structure change arising in the E-fraction of the fibrin monomer when the fibrin monomer generated in blood and fibrinogen form a complex. In the measuring method using this antibody, however, various proteins other than fibrinogen are present in blood, and therefore it is feared that the results of measurement are not accurate on account of the influence of proteins in blood (other than the fibrinogen) which associate with the fibrin monomer to form the complex. Moreover, in the measuring method using the present antibody, as the association-degree changes with the passage of time from the formation of the fibrin monomer to the generation of soluble fibrin, a change in its three-dimensional structure arises. For this reason, it is difficult to obtain a stable measurement because of change with the passage of time. Additionally, in the measurement for blood coagulation using the monoclonal antibody according to G. Soe et al., an epitope created by such a change in the three-dimensional structure does not emerge early in the blood coagulation, and further the antibody is not reactive with a native fibrin monomer generated in the blood.

Furthermore, in these conventional methods for assaying soluble fibrin, many of the antibodies used cross-react with fibrin decomposition products (XDP) in a body fluid, and thus it is difficult to say that they are specifically reactive with abnormal blood coagulation, in particular with an initial marker of diseases.

As described above, hitherto determination of blood coagulation in a living body, has used a monomer obtained by dissociating completed soluble fibrin by solubilization with a chemical agent or solubilized fibrin. There has not been known any assaying method using an antibody which can directly and simultaneously react with a fibrin monomer and soluble fibrin present in blood at the initiation of blood coagulation. An object of the present invention is to provide a monoclonal antibody for specifically detecting a native fibrin monomer produced at the initial stage of blood coagulation by the action of active thrombin, and detecting soluble fibrin simultaneously; a hybridoma which can produce the monoclonal antibody; and an immunoassay for assaying the initial stage of blood coagulation promptly, and with high sensitivity using the monoclonal antibody.

DISCLOSURE OF THE INVENTION

The present inventors have investigated use of a fibrin monomer analog in blood, as an immune source, to produce a monoclonal antibody which is not reactive with fibrinogen and can specifically and simultaneously recognize a native fibrin monomer and soluble fibrin. The native fibrin monomer is a fibrin monomer which is in a body fluid, in particular in blood, and is not solubilized. Herein, both the desAA-fibrin and the desAABB-fibrin are referred to as the fibrin monomer.

That is, the monoclonal antibody of the present invention is a monoclonal antibody which is specifically reactive with a native fibrin monomer, and at the same time is specifically and simultaneously reactive with a native, soluble fibrin wherein fibrinogen and a fibrin monomer are associated, even if a body fluid is used as a specimen, without being affected by the interaction of the fibrin monomer and admixed proteins other than the fibrinogen present in the body fluid.

The monoclonal antibody of the present invention is characterized by the aforementioned specific reactivity and not being reactive with various decomposition products of fibrin or fibrinogen, which are produced in a body fluid by cleavage by a plasmin.

The monoclonal antibody of the present invention makes it possible to directly assay a native-form substance to be detected, from the initial stage of blood coagulation, that is, the time when a fibrin monomer is produced, to the time when soluble fibrin is formed. This fact makes unnecessary solubilizing fibrin specimens for dissociation, as in the prior art. Therefore, operation efficiency, promptness and accuracy are improved in immunological assays. Furthermore, use of the monoclonal antibody of the present invention makes it possible to improve assay sensitivity since steps such as the step for solubilizing the fibrin specimen are unnecessary.

The method for producing a monoclonal antibody, according to the present invention, comprises fusing an antibody-forming cell obtained by using a fibrin monomer analog as an immune source to immunize an animal, and a myeloma cell by cell fusion, screening to obtain a hybridoma having antibody-forming ability exhibiting the desired reactivity, and establishing the hybridoma.

The reason why the fibrin monomer analog is used as an immune source is to obtain an antibody which is reactive with fibrin obtained by dissociating fibrinopeptide A in blood, that is, with both of a fibrin monomer and soluble fibrin in blood.

The reason why a native fibrin monomer itself is not used as an immune source in the production of the monoclonal antibody of the present invention is that the fibrin monomer in blood is associated with various blood proteins including fibrinogen, in blood, to form soluble fibrin, and consequently if the fibrin monomer itself is used an immune source, the possibility that an antibody specific to the fibrin monomer can be obtained is very low. Thus, the following method is considered: a fibrin monomer is purified from soluble fibrin and then the fibrin monomer is used as an immune source. For that, the soluble fibrin must be solubilized by a protein denaturant such as high-concentration urea or chaotropic ions. Since such protein denaturants change the three-dimensional structure of proteins, it is difficult to say that the resultant fibrin monomer is native. As a method for producing a fibrin monomer artificially without using any protein denaturant, a method using a coagulation inhibiting peptide is known. In this method, if thrombin is used to cleave fibrinopeptide A, which is a near native reaction, fibrinopeptide B is also cleaved. Namely, two types of complex formation inhibiting peptides become necessary for N-terminal cleavage sites in treatment of the fibrin monomer with thrombin, and thus the preparation becomes difficult.

The fibrin monomer analog in the present invention is defined as a substance which is similar to a fibrin monomer and is produced in body fluid by treating fibrinogen with an enzyme, a chemical agent or the like to dissociate fibrinopeptide. The number of amino acids of the dissociated fibrinopeptide is somewhat more or less than that of the fibrin monomer in body fluid, or the amino acids are substituted by other compounds. Preferably, the fibrin monomer analog in the present invention is fibrinogen treated with bathroxobin, which is a snake venom. Bathroxobin is specific in cleaving the peptide A of fibrinogen.

The reason why the monoclonal antibody of the present invention obtained by immunization by the fibrinogen treated with bathroxobin and cell fusion has the aforementioned specific reactivity would be presumably that even if by the reaction with an epitope present at a slightly internal site of the amino acid terminal of the active thrombin treated fibrinogen (that is, the fibrin monomer) the fibrin monomer is associated with the fibrinogen or other admixed proteins, the epitope is not masked.

In the method for producing the monoclonal antibody, according to the present invention, if the fibrinogen treated with the snake venom is used as is, it is associated with admixed proteins in a complex. If a complex-formation inhibiting peptide is added to this system, fibrinogen can fall in the state of fibrin monomer analog. Examples of the complex-formation inhibiting peptide used in the present invention include glycyl-prolyl-arginyl-proline, and glycyl-prolyl-arginyl-arginylsacrocine (ANDREW P. et al., Proc. Natl. Sci. USA, 1978).

In the screening in the method for producing the hybridoma of the present invention, antibody-forming cells are selected which are not reactive with either fibrinogen or fibrin decomposition products, and are reactive with the fibrin monomer analogs comprising fibrinogen treated with the snake venom, fibrinogen treated with thrombin, and soluble fibrin analogs obtained by further adding fibrinogen to the aforementioned fibrin monomer analog to become complexed therewith. In this screening step, substances to be screened are substances which are respectively immobilized on a plate for immunoenzyme assays. The fibrinogen treated with thrombin is a substance obtained by treating fibrinogen, immobilized on a plate, with thrombin.

In the cell fusion step in the method for producing the hybridoma of the present invention, if the antibody-forming cell and the myeloma cell are cells which can fuse, the animal of origin is not limited. From the viewpoint of cell fusion efficiency, however, it is preferred to use anti-forming cells and myeloma cells from the same sort of animal. As a cell fusion process, the process according to Kobler and Milstein (Nature 256, 495–497, 1975) can be used to produce a hybridoma producing an antibody having a desired specific reactivity.

The hybridoma of the present invention was deposited as Deposit No. FERM P-16276 with the Ministry of International Trade and Industry, Agency of Industrial Science and Technology, National Institute of Bioscience and Human Technology on Jun. 17, 1997 and transferred as Deposit No.. FERM BP-6386 to International Deposit based on the Budapest Treaty on June 17, 1998. All restrictions upon public access to the deposit will be irrevocably removed upon the grant of a patent on this Application and the deposit will be replaced if viable samples cannot be dispensed by the depository.

The present hybridoma can be cultured in vitro or in vivo to secrete a monoclonal antibody.

The monoclonal antibody of the present invention can be obtained by culturing the hybridoma obtained in the aforementioned manner in a test tube or in an abdominal cavity in an animal. The resultant antibody can be purified by a purifying method such as the protein A method, or ion-exchange chromatography. The immunoassay using the monoclonal antibody of the present invention comprises reacting a specimen containing a fibrin monomer which is present in a body fluid and is not solubilized with an immobilized monoclonal antibody which is not reactive with fibrinogen and is specifically reactive with the fibrin monomer, to assay fibrin in the body fluid. The immunoassay of the present invention is not limited to any special assay, and may be an assay based on any immunological binding using the monoclonal antibody of the present invention. Examples of a specimen to be assayed include any specimen which may contain a fibrin monomer (solubilized fibrin), in particular blood, plasma, serum, and urine.

As the immunoassay method, the following can be used: the EIA method of adsorbing at least one monoclonal antibody obtained according to the present invention onto a polystyrene plate, balls, magnetic particles or the like, adding a specimen thereto, and subsequently using an antibody labeled by an enzyme such as alkaliphosphatase, peroxidase, or alactosidase; the RIA method of using a radioactive isotope labeled antibody; and the FIA (florescent immunoassay) method of using a florescent antibody. Besides, the present invention can be applied to carrier agglutination assays which immobilize at least one antibody obtained according to the present invention on the surface of insoluble carrier particles (liposome, latex or the like) by chemical or physical bonding, mixing the antibody-immobilized carrier with a specimen, and measuring the amount of the resultant coagulation on a slide in or a cell. In this carrier agglutination assay preferably the speed of immunological reaction is measured at least two times as an increase in the absorbance after the reaction starts, so as to assay the amount of a native fibrin monomer or soluble fibrin, which are in a body fluid.

DESCRIPTION OF PREFERRED EMBODIMENTS

EXAMPLE 1

Figure 1:
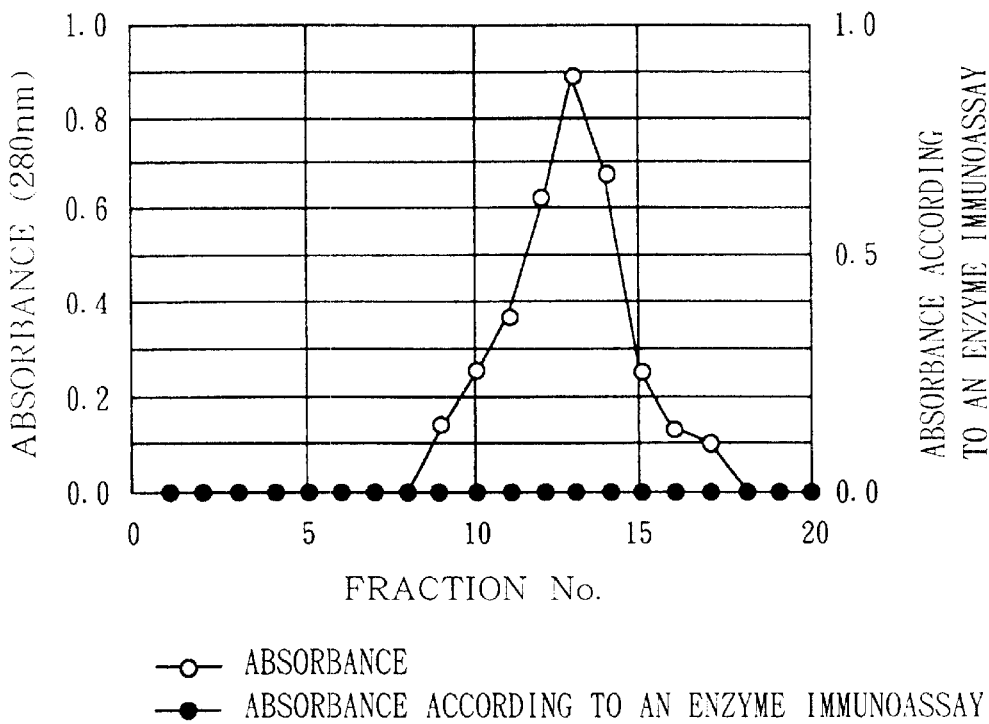
FIG. 1 shows reactivity of the monoclonal antibody of the present invention with soluble fibrin to which fibrinogen treated with thrombin is not added.

(1) Preparation of a Monoclonal Antibody
Preparation of Immunized Spleen Cells 100 ul of a 1 mg/ml snake venom-treated human fibrinogen (Desafib, manufactured by Biopool Co., Ltd.) as an immune source were mixed with Freund's complete adjuvant in the same amount so as to be emulsified, and then a BALB/C mouse of 4 week-age was subcutaneously immunized by the resultant mixture. Using Freund's complete adjuvant as a booster, the mouse was further immunized 2 times at intervals of 2 weeks in the same manner as above. After 14 days from the final immunization, and before 3 days from a cell fusion operation, 10 ug of an antigen were injected into the abdominal cavity of the mouse.

Cell Fusion

The spleen of the immunized mouse was aseptically extracted and then transferred on a culture dish to which a nylon mesh was fitted. The spleen was caused to pass through the mesh with a spatula. The resultant suspension of the spleen cells in the culture dish was collected in a 50 ml centrifugal tube, and further Dalbecco's phosphoric acid buffer was added thereto. The resultant mixture was subjected to centrifugation (1000 rpm×5 minutes) to wash the cells. This operation was carried out 3 times using the phosphoric acid buffer and 2 times using an RPMI 1640 medium, that is, 5 times in total. Thereafter, $1\times10^8$ of the mouse spleen cells were added to about $1\times10^7$ of mouse myeloma cells (NS-1, which is a known cell strain and can be purchased by anybody from cell handling makers, Eur. J. Immunolo., 6; 511–519, 1976) which were beforehand prepared and then mixed. Excess medium was removed by suction and subsequently 1 ml of a 50 % polyethylene glycol 4000 (trade name: polyethylene glycol the molecular weight of which was 4000, manufactured by Merck and Co., Inc.) solution which was kept at 37° C. was added to the solution wherein the spleen cells and the myeloma cells were mixed, and the resultant mixture was mixed for 2 minutes.

Next, an RPMI 1640 medium which was kept at 37 ° C. was slowly added thereto, and a washing operation was carried out 1 time. Further, the same medium was added hereto, and the resultant mixture was allowed to stand in a 5% $CO_2$ gas incubator at 37° C. for one hour. By a washing operation, the RPMI 1640 medium was substituted by a HAT medium, and then 200 ul of the resultant mixture were added into respective wells of 96-well plate for culturing cells so that the number of the spleen cells before cell fusion would be $1.5\times10^5$ and then were cultured in the 5% $CO_2$ gas incubator. During the cultivation, about 100 ul of the culture liquid were removed by suction at intervals of about few days, and then 100 ul of a new HAT medium were added thereto. Further, the cells were cultured for about one week. After the spleen cells and the myeloma cells which were not fused became extinct, the remaining cells were further cultured on a 10% fetal calf serum supplemented RPMI 1640 medium for 1–2 weeks to obtain hybridomas.

Selection of an Anti-human Fibrin Monomer Antibody Forming Hybridoma

A screening was carried out to select the hybridoma generating a desired antibody from the hybridomas obtained in the previous process. As a method for the screening, an enzyme immunoassay, which had been hitherto carried out, was used. As screening objects, the following S substances were selected: human fibrinogen, snake venom-treated human fibrinogen, a substance obtained by treating human fibrinogen with thrombin on a plate, a fibrin analog soluble in blood, obtained by further adding human fibrinogen to the plate, and a fibrin decomposition compound. The respective substances were immobilized on plates to prepare plates for enzyme immunoassay. A supernatant of the cultured hybridoma wherein colonies were generated was diluted 10–1000 times and the dilutions were added on the respective plates for enzyme immunoassay which were prepared in the previous step. After reaction for 1 hour and washing, the cultures were reacted with an alkaliphosphatase labeled anti-mouse IgG antibody for 1 hour. After further washing, a color development was performed to clone cells in the wells having an antibody which was not reactive with human fibrinogen or fibrin decomposition products and was reactive with all of the object substances.

Establishment of the Hybridoma

The cells in wells wherein the production of the desired antibody was confirmed by an enzyme immunoassay were transferred from the 96-well cell-culturing plates to 24-well cell-culturing plates to increase the number of the cells, and then the cells were cloned 2 times by limiting dilution. Finally, a hybridoma was obtained which was able to produce the antibody F405 which was not reactive with the human fibrinogen decomposition products, and was reactive with the snake venom treated human fibrinogen, the thrombin treated human fibrinogen, and the soluble human fibrin analog (that is soluble fibrin in vitro).

Production of a Monoclonal Antibody

Into the abdominal cavities of BALB/C mice was injected 0.5 ml of Pristane (2,6,10,14-tetramethylpentadecane, manufactured by Wako Pure Chemicals Industries, Ltd.). After about 1 week, the abdominal cavities were inoculated with $5 \times 10^6$ per mouse of the hybridoma cells cultured in vitro. After about 2 weeks, the ascites fluids of the mice were collected and then were primarily purified by the ammonium sulfate salting-out method. The once-purified fluids were secondly purified on a protein A column to obtain the antibody having an improved purity.

EXAMPLE 2

Confirmation of the Characteristics of the Monoclonal Antibody (i) Confirmation of the Immunoglobulin Class of the Monoclonal Antibody The reaction of various anti-mouse immunoglobulin class antibodies with the antibody F405 obtained in Example 1 was confirmed by Ouchterlony immunodiffusion to be of the class $IgG_1$.

(ii) Confirmation of Specificity to Various Antigens which were not Solubilized

To confirm the specificity of the antibody F405 obtained in Example 1, the antibody was immobilized on plates for enzyme immunoassay, and then thereto were added various antigens which had not been subjected to any solubilization such as urea-treatment or acid-treatment (that is, native antigens). After reaction for 1 hour, the plates were washed and then a POD labeled anti-human fibrinogen polyclonal antibody was added thereto. After further reaction for 1 hour, the plates were washed and then color-development of the enzyme was performed. The results thus obtained are shown in the following Table 1.

TABLE 1

| Antigens | F405 |
| --- | --- |
| Fibrinogen | − |
| DesAA-fibrin | + |
| DesAABB-fibrin | + |
| Fibrinogen fragment X | − |
| Fibrin fragment X | + |
| Fibrinogen fragment Y | − |
| Fibrin fragment Y | + |
| Fibrinogen fragment E | − |
| Fibrin fragment E | + |
| DD/E | − |
| DD | − |
| D | − |

In Table 1, "−" indicates lack of a positive reaction in the enzyme immunoassay, and "+" indicates a positive reaction in the enzyme immunoassay. These results demonstrated that the antibody F405 does not react with human fibrinogen and is reactive with only native human fibrinogen affected by active thrombin, or the substance derived from native human fibrinogen (soluble fibrin). Moreover, the DD/E and the DD, which are substances affected by the blood coagulation factor XIII, are not reactive, thus showing that the antibody F405 can specifically detect the coagulation. The fibrinogen shown in Table 1 was manufactured by MILES Co., Ltd., and the fibrinogen fragments X, Y, EE and DD were manufactured by CRYSTAL CHEM Co., Ltd. The DD/E and the DM were prepared in the ordinary manner.

(iii) Confirmation of the Reactivity with the Solubilized Antigens

Solutions wherein the respective antigens were solubilized by 5M urea and solutions wherein the respective antigens were treated with 50 mM acetic buffer (pH 3.5) were respectively subjected to centrifugation, so as to be divided into soluble fractions and insoluble fractions. The resultant respective soluble fractions were immobilized on plates for enzyme immunoassay. The antibody F405 obtained in Example 1 was added to respective wells of the plates on which the soluble fractions were immobilized.

After reaction at 25° C. for 1 hour, the plates were washed. An alkaliphosphatase labeled anti-mouse IgG antibody was added to the respective wells and then reaction at 25° C. was conducted for 1 hour. Furthermore, the plates were washed and then substrate solutions were added thereto. After reaction at 25° C. for 30 minutes, a color developing solution was added thereto to carry out assays at the main wavelength of 490 nm and the secondary wavelength of 650 nm. The results are shown in the following Table 2. For comparison, Table 2 also shows the reactivity of antibodies FM-1 and FM-2, according to G. Soe et al., which are known in public (WO/95/12617).

TABLE 2

| Antigens | FM-1 | FM-2 | FM-3 |
| --- | --- | --- | --- |
| Fibrinogen (treated with urea) | − | − | − |
| Fibrinogen fragment X (treated with urea) | − | − | − |
| Fibrinogen fragment Y (treated with urea) | − | − | − |
| Fibrinogen fragment E (treated with urea) | − | − | − |
| Fibrinogen fragment D (treated with urea) | − | − | − |
| deAA-Fbn (treated with urea) | − | + | + |
| deAA-Fbn (treated with an acid) | − | − | + |
| deBB-Fbn (treated with urea) | − | − | − |
| deBB-Fbn (treated with an acid) | − | − | − |
| deAABB-Fbn (treated with urea) | + | + | + |
| deAABB-Fbn (treated with an acid) | − | − | + |
| Fibrin fragment X (treated with urea) | + | + | + |
| Fibrin fragment X (treated with an acid) | − | − | + |
| Fibrin fragment Y (treated with urea) | + | + | + |
| Fibrin fragment Y (treated with an acid) | − | − | + |
| Fibrin fragment E (treated with urea) | + | + | + |
| Fibrin fragment E (treated with an acid) | − | − | + |
| DD/E (treated with urea) | + | + | − |
| DD/E (treated with an acid) | − | − | − |
| DD (treated with urea) | − | − | − |
| DD (treated with an acid) | − | − | − |
| Aα-chain 17–26 | − | − | + |
| Bβ-chain 15–24 | − | − | − |
| γ-chain 312–324 | − | − | − |
| A-chain (1–625) | − | − | − |
| B-chain (1–461) | − | − | − |
| γ-chain (1–411) | − | − | − |

In Table 2, "−" indicates lack of a positive reaction in the enzyme immunoassay, and "+" indicates a positive reaction in the enzyme immunoassay. These results demonstrated that the monoclonal antibody F405 of the present invention is reactive with the fibrinogen obtained by dissociating the fibrinopeptide A, and its decomposition products, regardless of whether or not the solubilization of the antigens was carried out. The fibrinopeptide A was dissociated but it was confirmed that the fibrinopeptide A was not reactive with the DD/E fraction which was crosslinked by the blood coagulation factor XIII.

Reactivity with Soluble Human Fibrin

Human fibrinogen was converted into fibrin monomers by adding to the human fibrinogen (1 mg/ml) thrombin (0.1 U/ml) in such a little amount that no coagulation was produced. Next, the resultant human fibrin monomers (1 mg/ml) were added to 5 mg/ml of human fibrinogen, so as to obtain soluble human fibrin prepared artificially. The resultant soluble human fibrin was subjected to molecular sieve chromatography using an FPLC system of Pharmacia Co., Ltd., so as to be separated into fractions. The absorbance of the respective fractions was measured, and the reactivity of the F405 with soluble human fibrin was confirmed using an enzyme immunoassay (the same manner as in the specification test). The results are shown in the graphs of FIGS. 1 and 2.

Figure 2:
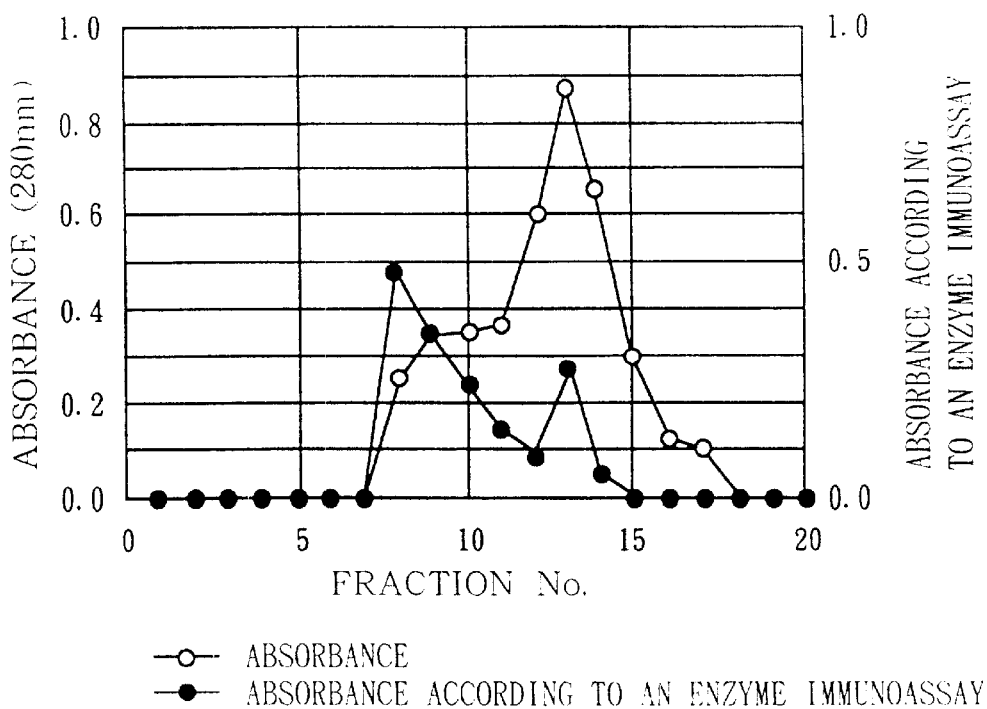
FIG. 2 shows reactivity of the monoclonal antibody of the present invention with soluble fibrin to which fibrinogen treated with thrombin is added.

FIG. 1 shows the results for the sample to which no thrombin-treated human fibrinogen was added, and FIG. 2 shows the results for the sample to which 100 ug of the thrombin-treated human fibrinogen were added. In FIGS. 1 and 2, the X axes (abscissa) show fraction numbers, the (left) Y axes (ordinates) show absorbance at a wavelength of 280 nm (○) and the (right) Y axes (ordinates) show the measured values (absorbance) obtained by the enzyme immunoassay using the antibody F405 (●).

As compared with the sample which is shown in FIG. 1 and to which thrombin-treated human fibrinogen was not added, soluble fibrin was able to be recognized at higher molecular weights relative to the main peak, in the sample which is shown in FIG. 2 and to which the same was added. The antibody F405 did not exhibit reactivity with any fraction shown in FIG. 1, but exhibited reactivity with soluble human fibrin.

Reactivity with Ordinary Specimens

To examine the reactivity of the present antibody with soluble fibrin in real specimens, the amount of fibrin was measured by a commercially available FM assay reagent (Boehringermannheim Co. Ltd., Enzymum test FM), and then 5 specimens of ordinary plasma to which the measured values were attached were assayed by an enzyme immunoassay using the antibody F405 as follows. The antibody F405 was diluted by a phosphoric acid buffer to be 10 ug/ml, and then 100 ul of the dilution were poured into respective wells of an immunomodule of Nunc Inc. After reaction at 37° C. for 30 minutes, the plate was washed 3 times with a phosphoric acid buffer. Next, 200 ul of a 0.5% BSA-containing phosphoric acid buffer was poured into the respective wells for blocking of the plate (for preventing nonspecific reaction), and then reaction was allowed to continue at 37° C. for 30 minutes to prepare an antibody F405 immobilized plate for enzyme immunoassay. In the assay of the specimens, 5 ul of the specimens were beforehand diluted by 1000 ul of a 0.5% BSA-containing phosphoric acid buffer, and 100 ul of the specimen dilutions were added to the respective wells of the antibody F405 immobilized plate for enzyme immunoassay reaction at 25° C. for 60 minutes. Next, the plate was washed 3 times with a phosphoric acid buffer, and then to the respective wells were added a solution wherein a peroxidase labeled antifibrinogen polyclonal antibody (manufactured by DAKO Inc.) was diluted 1000 times by a 0.5% BSA-containing phosphoric acid buffer, to allow reaction at 25° C. for 60 minutes. After the plate was further washed 3 times by a phosphoric acid buffer, 100 ul of a solution of a diammonium salt of 2,2'-azino-bis (3-ethylbenzthiazoline-6-sulfonic acid) were added to the respective wells as a color developer to allow reaction at room temperature for about 10 minutes. Thereafter, their absorbance was measured at a wavelength of 405 nm to obtain the results shown in the following Table 3.

TABLE 3

|  | Amount of Fibrin (ug/ml) | Measured values in F405 enzyme immunoassay (absorbance) |
| --- | --- | --- |
| Specimen A | 10.4 | 0.124 |
| Specimen B | 19.5 | 0.162 |

TABLE 3-continued

|  | Amount of Fibrin (ug/ml) | Measured values in F405 enzyme immunoassay (absorbance) |
| --- | --- | --- |
| Specimen C | 123.5 | 0.294 |
| Specimen D | 126.5 | 0.300 |
| Specimen E | 771.4 | 0.346 |

From the results shown in Table 3, it was confirmed that the amount of human fibrin in blood (soluble fibrin) can be measured, without solubilizing the specimen, by using the antibody F405.

Assay Sensitivity of Non-treated Specimens

By an enzyme immunoassay using the antibody F405 of the present invention, an examination of the difference in reactivity between solubilized specimens and non-solubilized specimens was made as follows. Using 5 ordinary specimens which were positive for human fibrin, the non-solubilized specimens were assayed in the same manner as described above under the heading "Reactivity with ordinary specimens," and solubilized specimens were assayed as follows. At the time of diluting the specimens, 100 ul of a mixed solution of 5M NaI and 0.98 M KSCN were added to 5 ul of the specimens. After reaction at 25° C. for 30 minutes, the resultant mixture was diluted by 900 ul of a 0.5% BSA-containing phosphoric acid buffer. Thereafter, 100 ul of the resultant specimen dilution were added to each of the wells of the antibody F405 immobilized plate for enzyme immunoassay to carry out assays. (Subsequent steps were the same as in the case of assaying the non-solubilized specimens.) As a result, the results shown in the following Table 4 were obtained.

TABLE 4

|  | Solubilized specimen | Non-solubilized specimen | Magnification of a rise in assay sensitivity |
| --- | --- | --- | --- |
| Specimen F | 0.372ABS | 0.794ABS | 2.13 times |
| Specimen G | 0.386ABS | 1.047ABS | 2.71 times |
| Specimen H | 1.102ABS | 1.985ABS | 1.80 times |
| Specimen I | 0.601ABS | 1.157AB5 | 1.93 times |
| Specimen J | 0.493ABS | 0.784AB5 | 1.56 times |

As shown in Table 4, the assay system wherein the solubilization of the specimens is unnecessary can show assay sensitivity about 1.5–2.7 times as high as that of the assay system wherein it is necessary.

Industrial Availabilty

The monoclonal antibody of the present invention makes it possible to specifically detect a native fibrin monomer (that is, a fibrin monomer which is not subjected to solubilization such as treatment with urea or an acid) produced at the initial stage of blood coagulation by the action of thrombin, and simultaneously detect soluble fibrin, without the interference by various decomposition products of fibrin or of fibrinogen. Therefore, it is possible to detect the initial stage of blood coagulation with high sensitivity, quickly, efficiently and accurately.

What is claimed is:

1. An isolated or purified monoclonal antibody, which is obtainable by using a fibrin monomer analog as an immune source, and which is not reactive with fibrinogen and is specifically reactive with native desAA fibrin monomer, with native desAABB fibrin monomer, and with soluble fibrin, said fibrin monomers being present in a body fluid and not solubilized by treatment with urea or acid, said monoclonal antibody secreted by a hybridoma deposited as FERM BP-6386.

2. The isolated or purified monoclonal antibody according to claim 1, wherein the monomers are obtained by treating fibrinogen with bathroxobin, which is a snake venom.

3. The isolated or purified monoclonal antibody according to claim 1, which is not reactive with decomposition products of either fibrin or fibrinogen which are produced in a body fluid by reaction with plasmin.

4. An isolated or purified hybridoma, deposited as FERM BP-6386, which secretes a monoclonal antibody according to claim 1.

5. A method for producing a monoclonal antibody, which comprises:

administering to an animal a fibrin monomer analog obtainable by treating fibrinogen with bathroxobin as an immune source;

recovering the animal cells which produce antibodies to the fibrin monomer analog;

fusing the recovered cells with myeloma cells to produce said hybridoma which can secrete a monoclonal antibody according to claim 1;

culturing the resultant hybridoma in a medium or an animal; and isolating the monoclonal antibody from the medium or the animal.

6. An immunoassay, which comprises:

(a) reacting a specimen containing a native fibrin monomer which is present in a body fluid, and is not solubilized, with an isolated or purified immobilized monoclonal antibody which is not reactive with fibrinogen and is specifically reactive with native desAA fibrin monomer, native desAABB fibrin monomer and soluble fibrin, (b) forming a complex between said monoclonal antibody and at least one of said native desAA fibrin monomer, native desAABB fibrin monomer and soluble fibrin, (c) correlating the complex formed in step (b) to the presence of native desAA fibrin monomer, native desAABB fibrin monomer and soluble fibrin in the body fluid, said monoclonal antibody secreted by a hybridoma deposited as FERM BP-6386.

7. The immunoassay according to claim 6, wherein the immobilized monoclonal antibody is immobilized on insoluble carrier particles, and the assay of fibrin monomers and soluble fibrin is by measurement of an increase in absorbance.

8. The immunoassay according to claim 6, wherein the monoclonal antibody is at least one kind of monoclonal antibody.

9. The monoclonal antibody produced by the method of claim 5.

* * * * *